United States Patent
Vilasi et al.

(10) Patent No.: US 10,391,272 B1
(45) Date of Patent: Aug. 27, 2019

(54) EXPANDABLE INTER-VIVOS TUBE

(71) Applicants: Joseph A. Vilasi, Lakewood Ranch, FL (US); John V. Vilasi, Bradenton, FL (US); Joseph D'Ambrosio, Ridgefield, CT (US)

(72) Inventors: Joseph A. Vilasi, Lakewood Ranch, FL (US); John V. Vilasi, Bradenton, FL (US); Joseph D'Ambrosio, Ridgefield, CT (US)

( * ) Notice: Subject to any disclaimer, the term of this patent is extended or adjusted under 35 U.S.C. 154(b) by 0 days.

(21) Appl. No.: 16/179,908

(22) Filed: Nov. 3, 2018

Related U.S. Application Data

(60) Provisional application No. 62/732,402, filed on Sep. 17, 2018.

(51) Int. Cl.
 *A61M 16/04* (2006.01)

(52) U.S. Cl.
 CPC .... *A61M 16/0488* (2013.01); *A61M 16/0409* (2014.02); *A61M 16/0431* (2014.02); *A61M 2205/0216* (2013.01); *A61M 2240/00* (2013.01)

(58) Field of Classification Search
 CPC .............. A61M 16/04; A61M 16/0488; A61M 16/0402; A61M 16/0409; A61M 16/0418; E03B 7/10
 USPC .................. 138/28; 623/1.2, 1.17, 1.15, 1.12
 See application file for complete search history.

(56) References Cited

U.S. PATENT DOCUMENTS

| | | | |
|---|---|---|---|
| 4,722,335 A | 2/1988 | Vilasi | |
| 5,647,358 A | 7/1997 | Vilasi | |
| 2005/0224079 A1 | 10/2005 | Green | |
| 2008/0078399 A1 | 4/2008 | O'Neill | |
| 2008/0078405 A1* | 4/2008 | Crumback | A61M 16/04 128/207.15 |
| 2010/0313894 A1 | 12/2010 | Crumback | |
| 2012/0109179 A1 | 5/2012 | Murphy | |
| 2014/0102459 A1 | 4/2014 | Vilasi | |
| 2014/0116446 A1 | 5/2014 | Vilasi | |
| 2014/0213969 A1 | 7/2014 | Vilasi | |
| 2014/0238405 A1 | 8/2014 | Vilasi | |
| 2014/0345622 A1 | 11/2014 | Vilasi | |
| 2015/0001828 A1 | 1/2015 | Vilasi | |

* cited by examiner

*Primary Examiner* — Timothy A Stanis
(74) *Attorney, Agent, or Firm* — Law Office of Carl Giordano, PC

(57) ABSTRACT

An expandable inter-vivos tube that allows for a single size to be used for adult or pediatric intubation is disclosed. The inter-vivos tube comprises a tube and a slit extending from a proximal end to a distal end of the tube. An adjustment means provides for the expansion of the tube to contact the glottis area preventing the back flow of inspired gases from escaping the patient.

17 Claims, 10 Drawing Sheets

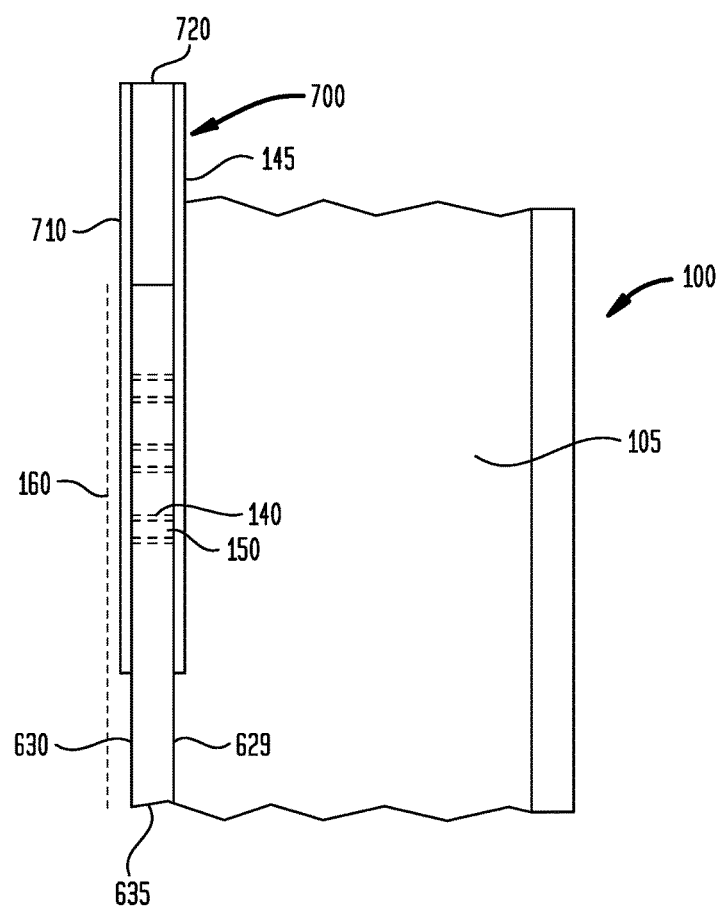

US 10,391,272 B1

EXPANDABLE INTER-VIVOS TUBE

CLAIM OF PRIORITY

This applicant claims, pursuant to 35 USC 119, priority to and the benefit of the earlier filing date of that patent application filed on Sep. 17, 2018 and afforded Ser. No. 62/732,402, the contents of which are incorporated by reference, herein.

FIELD OF THE INVENTION

This invention is related to the field of medical devices and more particularly, to expandable inter-vivos tubes and means for controlling the expansion of same.

BACKGROUND OF THE INVENTION

Inter-vivos tubes, when inserted within a patient, are used to provide an air passage to sedated patients, who are unable to autonomously breath. Conventional inter-vivos tubes or endotracheal tubes (ETT) consist of a long hollow tube with an inflatable cuff balloon near the distal end of the long hollow tube. A smaller channel, within the wall of the long hollow tube connects to the inflatable cuff balloon and provides air to the balloon to expand the balloon to engage walls of the patient's trachea. When the cuff balloon is inflated, confirmation of a leak free contact with the trachea is determined, and delivery of anesthetic gases and oxygen then proceeds.

In the conventional inter-vivos tubes, the tubes are extended past the vocal cords so that a distal end of the inter-vivos tube is contained within the trachea passage. The balloon element (i.e., a cuff), located at or near a distal end of the inter-vivos (i.e., a distal cuff) tube is then expanded to prevent air (or gas) administered through the inter-vivos tube from escaping upward toward the mouth while the administered air (or gas) is directed directly toward the sedated patient's lungs.

Conventional ETT vary in size and are numbered according to the internal diameter (ID). In children the internal diameter varies from 3.5 to 7 mm and in adults from 7-11 mm. Ideally the ETT diameter should approximate closely the glottic size of the patient as the tube must past through the vocal cords to allow the cuff balloon to expand toward the trachea walls.

However, as there is no way to estimate the glottic size (or vocal cord size) prior to intubation, an ETT selected for a patient is determined based on the sex, height, and weight of the patient and the experience of the person inserting the ETT into the patient. The distal inflatable cuff incorporated into present day ETTs compensate for any mis-sizing of a selected ETT by compressing the tracheal wall to establish a closed circuit inflow from the anesthesia machine and outflow from the patient's lungs to the exhalation value.

However, if the circumference of the selected ETT is too small then the flow of air or gas to patient is restricted. That is, the smaller circumference of the ETT, in relation to the size of the glottis, creates increased gas flow resistance, especially when the patient is ventilating spontaneously. This resistance is in a range from 35 to 100 percent. In pediatric procedures, where a cuffed tube is particularly undesirable and to avoid pressure on the vasculature of a particularly delicate tracheal wall, a "Cole" funnel shaped tube is often used to create an air leak-free flow.

In addition, it is known in the medical art that the endotracheal tube cuff contacting the trachea may result in damage to the patient's trachea as the cuff presses against delicate tissues within the trachea walls.

Some of the drawbacks of present day ETTs are the necessity of constructing a longer endotracheal tube that has to extend well into the trachea with an expandable distal cuff that compresses against the tracheal wall. The ischemic compression of tracheal wall capillaries, caused by the expanded distal cuff, often results in the well-documented inflammation of the tracheal wall and diminished capillary activity.

In addition, conventional cuffed ETTs often contribute to the well-known problem of Ventilator Associated Pneumonia (VAT) that is generally attributable to the inflated cuff contacting the trachea and complicating post-operative recovery. The occurrence of VAT in patients increases the cost associated with surgery.

Hence, there is a need in the industry an expandable inter-vivos tube that overcomes the drawbacks occurring with the use of conventional inter-vivos (endotracheal) tube design.

SUMMARY OF THE INVENTION

It is an object of the instant invention to provide a new and inventive design for an expandable inter-vivos tube and a corresponding cap design that is applicable to the inter-vivos tubes that allows for the expansion/contraction of the tube without incurring the problems of conventional ETTs.

In one aspect of the invention, an expandable inter-vivos tube is constructed with at least one slit extending along a longitudinal axis of a tube element. Each of the at least one slit forming opposing edges that substantially abut one another when in the closed position. The tube element being composed of known material (e.g., human gradable flexible plastic) similar to materials used in conventional inter-vivos tubes. On opposing sides of the at least one slit are slots or grooves oriented at an acute angle with respect to a corresponding one of the at least one silt, wherein the angle is measured with respect to a proximal end of the tube element.

In another aspect of the invention, a slidable mechanism, associated with each of the at least one slit, is incorporated within the inter-vivos tube and extends above a proximal end of the inter-vivos tube. The slide able mechanism further includes a plurality of pins (nipples or nibs) that extend through a corresponding one of the slots or grooves within the tube element.

In one aspect of the invention, the plurality of pins, nipples or nibs, extending through a corresponding one of the slots or grooves, is positioned at a proximal end of the corresponding one of the slots or grooves. In accordance with the principles of the invention, the plurality of pins (nipples or nibs) are positionable within a corresponding one of the slots or grooves between the proximal end and a distal end of the corresponding one of the slots or grooves. The positioning of the nipples determining an expansion of the inter-vivos tube.

In accordance with the principles of the invention, as the slidable mechanism is moved or pushed toward a distal end of the inter-vivos tube, the plurality of pins within a corresponding one of the slots or grooves slide between the proximal end of the corresponding one of the slots or grooves toward the distal end of the corresponding one of the slots or grooves to expand the distance between the edges of a corresponding one of the at least one slit.

In another aspect of the invention, a cap engages the proximal end of the slidable mechanism to allow for the movement of the slidable mechanism by the application of a downward force onto the slidable mechanism.

In another aspect of the invention, a flange may be incorporated substantially near a proximal end of the inter-vivos tube to allow for the application of an upward force to be applied to the tube element as a downward force is applied to a cap.

In another aspect of the invention, the cap may include a screw thread mechanism that controls a downward force applied to the proximal end of the slidable mechanism.

In another aspect of the invention, the cap may include a nib or ridge that engages a groove within the slidable mechanism. The nib may then be used to apply a downward force on the slidable mechanism to lower the slidable mechanism or an upward force to raise the slidable mechanism. The internal circular ridge near the end of the cap has the same thickness as the slidable mechanism.

BRIEF DESCRIPTION OF THE DRAWINGS

For a better understanding of exemplary embodiments and to show how the same may be carried into effect, reference is made to the accompanying drawings. It is stressed that the particulars shown are by way of example only and for purposes of illustrative discussion of the preferred embodiments of the present disclosure, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. It would be further recognized that the accompanying drawings are not drawn to scale. In the accompanying drawings:

FIG. 7 illustrates a cross-sectional view, along a longitudinal axis, of a second embodiment of a sliding mechanism is accordance with the principles of the invention.

It is to be understood that the figures and descriptions of the present invention described herein have been simplified to illustrate the elements that are relevant for a clear understanding of the present invention, while eliminating, for purposes of clarity many other elements. However, because these omitted elements are well-known in the art, and because they do not facilitate a better understanding of the present invention, a discussion of such element is not provided herein. The disclosure herein is directed to also variations and modifications known to those skilled in the art.

BRIEF DESCRIPTION OF THE INVENTION

Figure 1A:
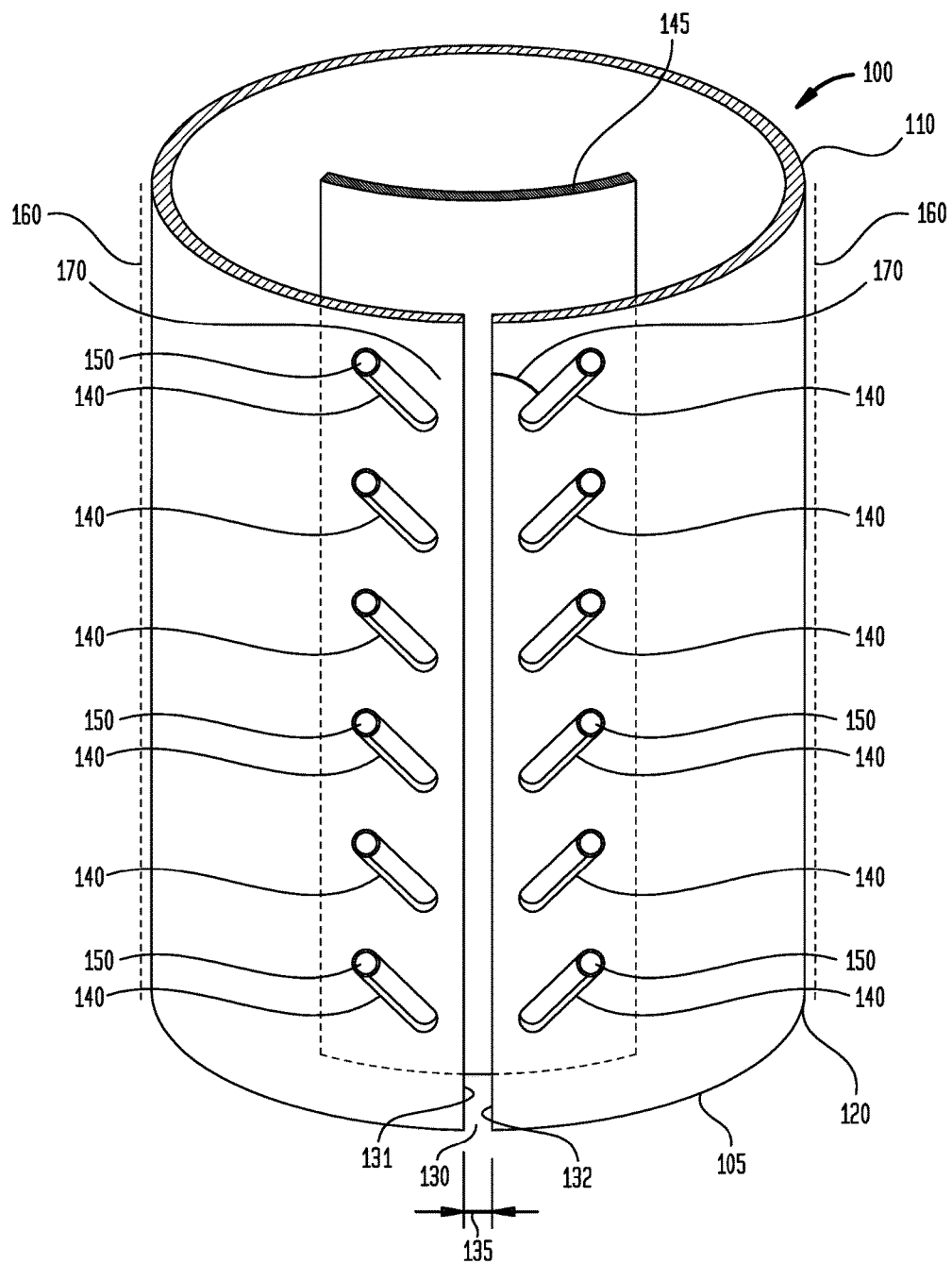
FIG. 1A illustrates a perspective view of an exemplary first aspect of an inter-vivos tube in accordance with the principles of the invention.
Figure 1B:
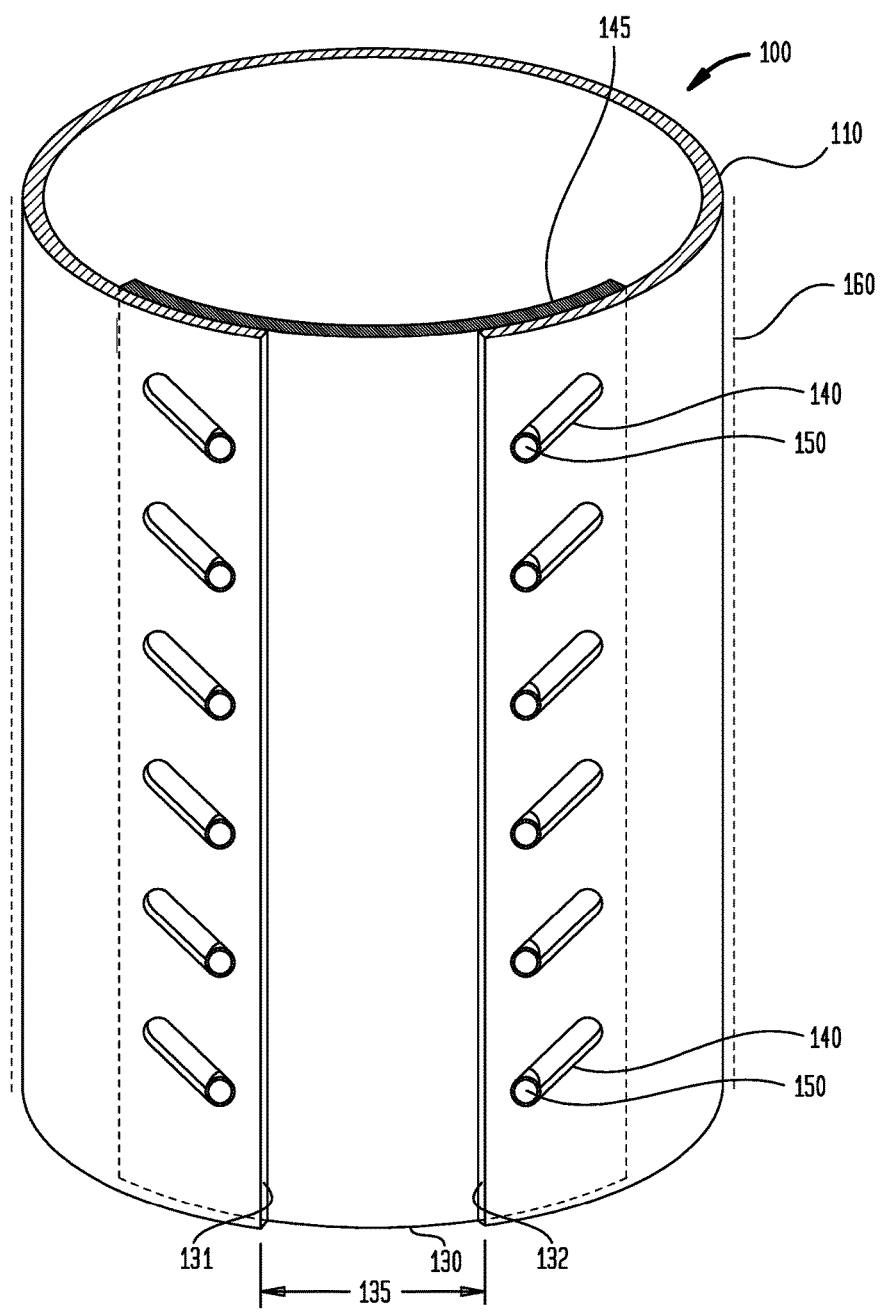
FIG. 1B illustrates a perspective view of an exemplary second aspect of an inter-vivos tube in accordance with the principles of the invention.

FIGS. 1A and 1B illustrate a perspective view of an inter-vivos tube (ETT, hereinafter) in accordance with the principles of the invention.

FIG. 1A illustrates an inter-vivos tube 100 comprising a tube element 105 and at least one slit 130 within the tube element 105, extending along a longitudinal axis of the tube element 105, from a proximal end 110 to a distal end 120 of tube element 105. Each of the at least one slit 130 forming opposing edges 131,132 that substantially abut one another when in the closed position.

Further illustrated is a plurality of slots or grooves 140 arranged on opposing sides of a corresponding one of the at least one slit 130. The slots or grooves 140 are arranged at an acute angle 170 (measured with respect to the longitudinal axis and proximal end 110) with a corresponding one of the at least one slit 130.

Further illustrated is a sliding mechanism 145, positioned along an interior surface of the tube element 105 extending, initially above the proximal end 110 of tube element 105. Sliding mechanism 145 is arranged to span a corresponding one of the at least one slit and includes a plurality of nipples 150 (pins, nibs) extending through a corresponding one of slot or groove 140, wherein in the illustrated embodiment, are positioned at a proximal end of a corresponding slot. That is, in the initial configuration (i.e., the closed position with the edges 131, 132 substantially abutting each other), the nipples are arranged at a proximal end of a corresponding slot.

Further illustrated is a sheathing, cuff membrane or membrane element 160 formed tightly about tube element 105. Sheathing 160 is an expandable membrane that provides a smooth outer surface for inter-vivos tube 100. As would be appreciated, the membrane element 160 may be sealed substantially near the proximal end 105 and near the distal end 120 to create an air-tight inter-vivos tube 100 configuration, wherein as tube element 105 expands, the membrane element 160 expands along with the expanding tube element.

In accordance with the principles of the invention, the inter-vivos tube 100 shown in FIG. 1A is shown in a contracted, closed or initial configuration. In this illustrate embodiment, the separation 135 of the edges 131, 132 of slit 130 is at a minimum distance. That is, edges 131, 132 substantially abut one another without any overlap.

FIG. 1B illustrates the inter-vivos tube 100 shown in FIG. 1A in accordance with a second aspect of the invention.

In this illustrated aspect, the sliding mechanism 145 is pushed downward such that the nipples 150, shown in corresponding slots 140, are shifted downward to a distal end of each of a corresponding slot 140.

In accordance with the principles of the invention, as sliding mechanism 145 is pushed downward, nipples 150 are forced to move downward in a corresponding slot 140. And as nipples 150 move downward, the angle of the slots 140 with respect of the at least one slit 130, causes a corresponding one of the at least one slit 130 to expand such that the distance 135 between edges 131, 132 of corresponding at least one slit increases. The increased distance 135 causes the inner diameter of tube 105 to increase.

In this illustrated example, the inter-vivos tube 100 is shown in an expanded configuration, wherein the separation of the edges 135 of slit 130 is at a maximum.

In accordance with the principles of the invention, the expandable inter-vivos tube disclosed may expand from an initial configuration (e.g., 6 mm internal diameter) to a maximum configuration (e.g., 12 mm internal diameter).

Although, a single slit 130 is shown, it would be recognized that a plurality of slots 130 may be incorporated into tube element 105 without altering the scope of the invention claimed. For example, if the number of slots 130 is increased to 2, the slots 130 may be positioned diametrically opposed to one another (i.e., 180 degree separation) in tube element 105. Similarly, if the number of slots 130 is three, the slots may be positioned at a separation angle of 120 degrees. And if the number of slots is further increased to 4, then slots may be positioned at a separation angle of 90 degrees.

Accordingly, with an increase number of slots 130 incorporated into tube element 105, the spacing of each of the at least one slit 130 needed to expand inter-vivos tube 100 from a minimum configuration to a maximum configuration is reduced.

Although, the angular separation of the at least one slit 130 within tube element 105 is discussed as being substantially uniform, it would be further recognized that the orientation of the at least one slit 130 within tube element 105 may be selected based on a desired direction of expansion. That is, the spacing between adjacent slits may be of a first value to allow for an expansion in a first direction and the spacing between other adjacent slits may be of a second value to allow for a different degree of expansion in a second direction.

Figure 2:
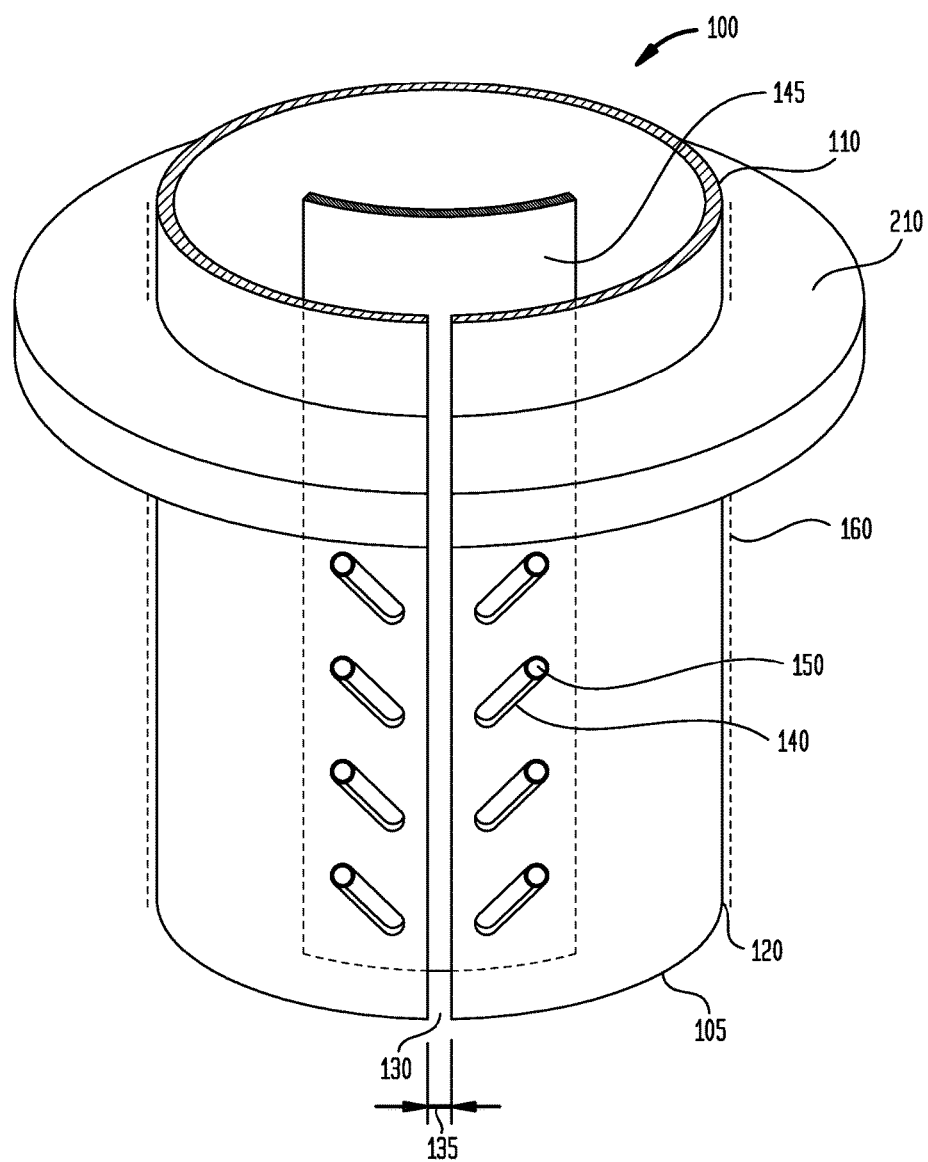
FIG. 2 illustrates a perspective view of a second embodiment of the inter-vivos tube shown in FIG. 1A.

FIG. 2 illustrates a second embodiment of the inter-vivos tube 100 shown in FIG. 1A.

In this illustrated embodiment, inter-vivos tube 100 is similar to that shown in FIG. 1A in an initial or contracted configuration, wherein distance 135 between edges 131, 132 of the illustrated at least one slit 130 is a minimum distance (e.g., substantially zero).

Inter-vivos tube 100 comprised of tube element 105 and at least one slit 130 further includes slots or grooves 140 into which pins 150 of sliding mechanism 145 are inserted, as previously discussed.

Further illustrated is a flange member 210 incorporated substantially near the proximal end 110 of tube element 105.

Flange member 210 provides for a finger grip that allows an upward pressure (or force) to be applied to the flange member 210 as a downward pressure (or force) is applied to sliding mechanism 145. Flange member 201 may be sized to accommodate the expansion of tube element 105 and may be attached to tube element 105 by an elastic member or other type of attachment means (e.g., VELCRO, VELCRO is a registered trademark of Velcro Industries B.V. Netherlands).

Figure 3:
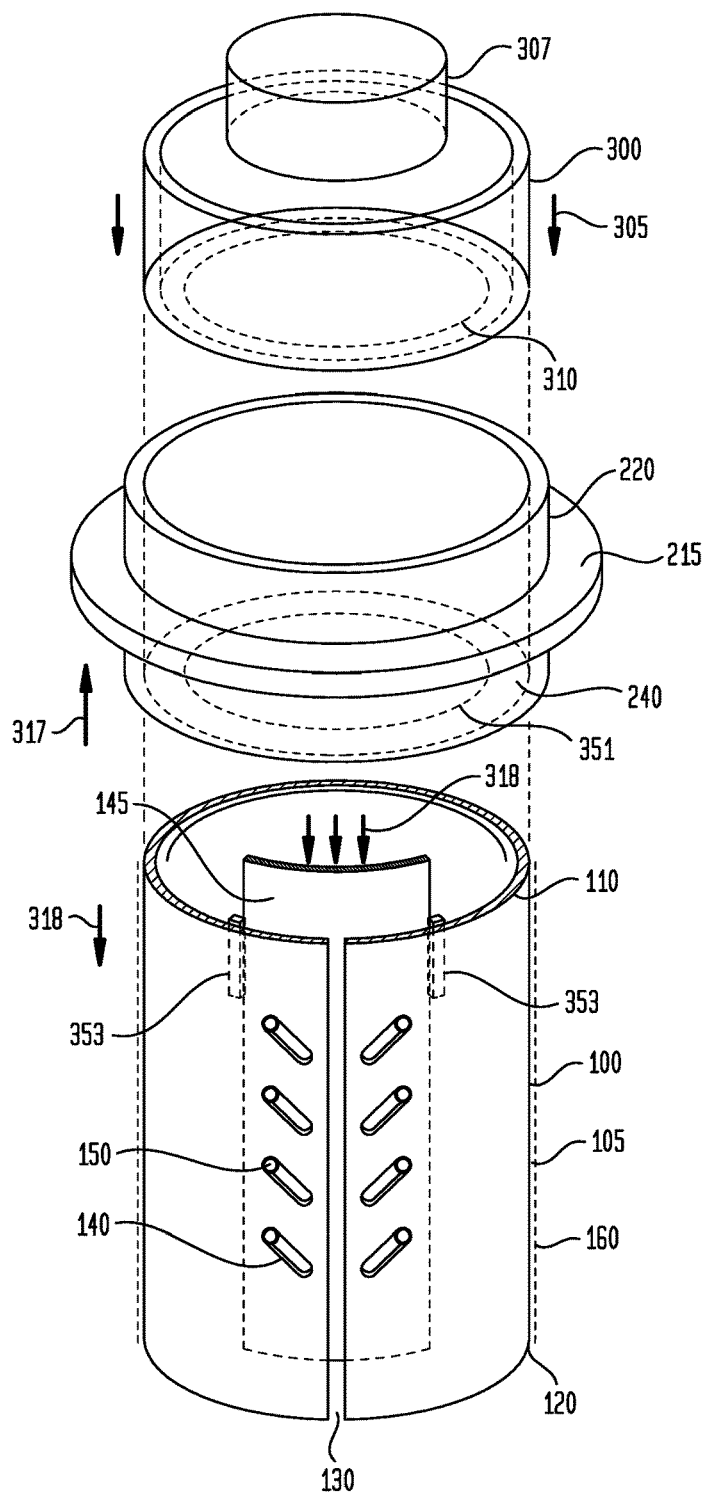
FIG. 3 illustrates a perspective view of a first embodiment of a control system for controlling the expansion of the inter-vivos tube shown in FIG. 1A.

FIG. 3 illustrates a first embodiment of an expanding control system incorporating the inter-vivos tube 100 shown in FIG. 1A.

In this illustrated embodiment, inter-vivos tube 100 is similar to that shown in FIG. 1A in its initial or contracted configuration wherein the distance 135 between edges 131, 132 of the at least one slit 130 is a minimum, non-overlapping, or abutting, distance (e.g., zero).

Further illustrated is a cap element 220, which includes a flange member 215, circumventing cap element 220, incorporated substantially near a distal end of cap element 220

Cap element 220 is sized to fit over proximal end 110 of tube element 105 and is sized to accommodate a full expansion of inter-vivos tube 100. Cap element 220 may be held in place on a contracted inter-vivos tube 100 by a tape or other means (e.g., a VELCRO fastener) to allow inter-vivos tube 100 to expand within cap element 220.

With cap element 220 attached to a proximal end 110 of tube element 105, flange member 215 provides a finger grip that allows an upward force (as represented by arrow 317) to be applied to flange member 215, while a downward pressure or force (as represented by arrows 318) is applied to a proximal end of sliding mechanism 145.

Further illustrated is expandable membrane 240 (i.e., a diaphragm) positioned to span a distal end of cap 220, into which inter-vivos tube 100 may be inserted. Membrane 240, which includes a center hole 351, allows for the insertion of inter-vivos tube 100 into cap element 220, and provides an air tight fit between cap element 220 and inter-vivos tube 100.

In accordance with the principles of the invention, the cap element 220 may be composed of a rigid material or an expandable material that allows for an increase in the size of the cap 220 as the tube element 105 increases in size.

In accordance with the principles of the invention, the cap element 220 may be slide onto tube element 105 to be attached to, or integrated, with tube element 105.

Further illustrated is expansion control element 300. Control element 300 is insertable into cap element 220. Expansion control element 300 includes an interior ring or ridge element 310 that is configured to engage a top (or proximal) edge of sliding mechanism 145 within inter-vivos tube 100 inserted through membrane 240.

In accordance with the principles of the invention, as expansion control element 300 is pushed downward, as illustrated by arrows 305, a downward force (as represented by arrows 318) is applied to a top or proximal edge of slider mechanism 145 by the inner ring or ridge element 310. The downward force causes sliding mechanism 145 to move downward within tube element 105 so that nipples or tabs 150, within slots 140, correspondingly move from their position in a proximal end of a correspond slot to a distal end of a corresponding slot. The downward moving nipples or tabs 150 cause corresponding one of the at least one slit 130 to expand and increase the circumference of the inter-vivos tube 100.

In this illustrated example, the expansion control element 300 further includes an adapter 307 that allows for the connection of conventional tube elements through which a gas or air may be provided.

Further illustrated are ridges 353 positioned along an interior surface of tube element 105, wherein slider 145 is contained therebetween. Ridges 353 retain slider 145 substantially straight as a pressure or force is applied to the proximal end of slider 145.

Figure 4:
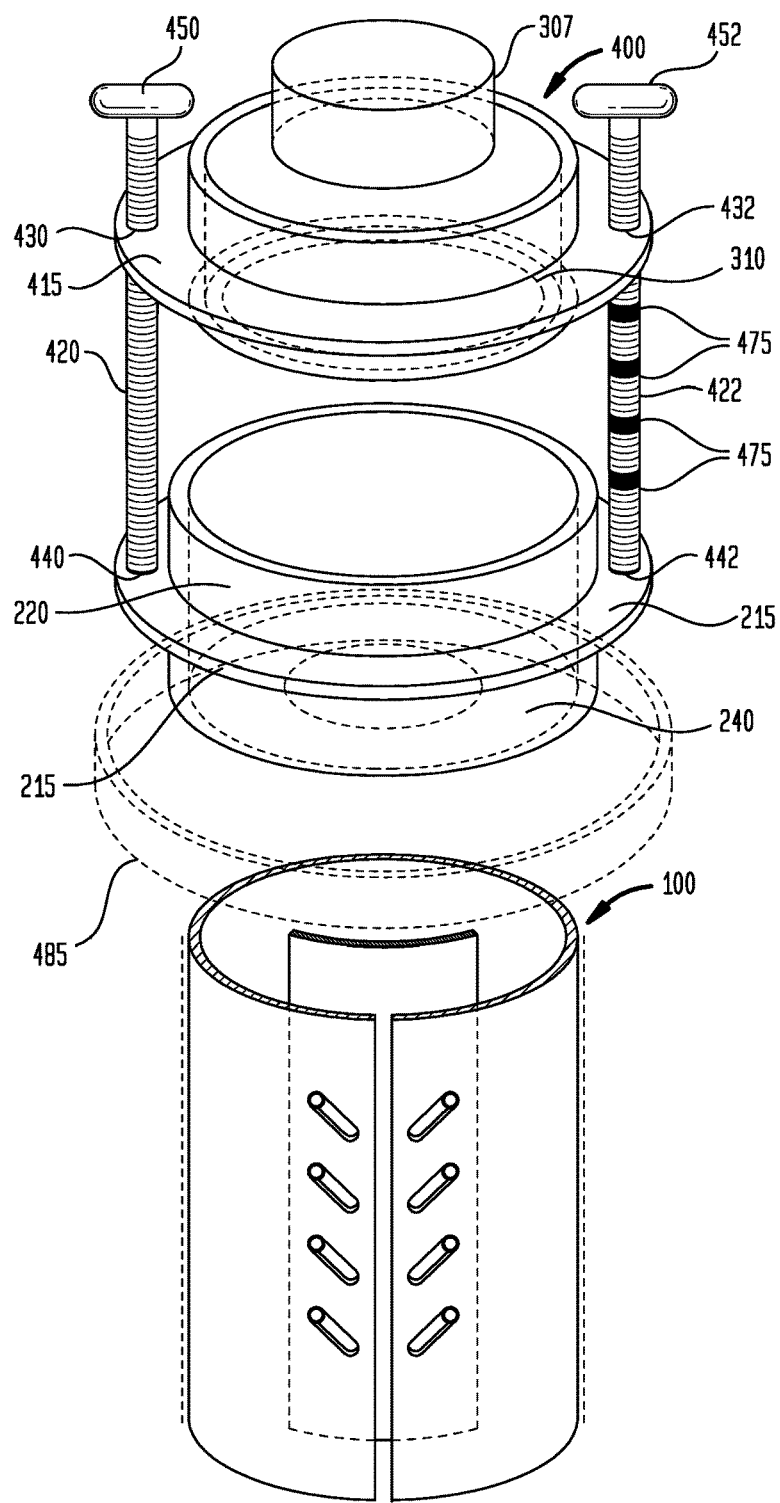
FIG. 4 illustrates a perspective view of a second embodiment of a a control system for controlling the expansion of the inter-vivos tube shown in FIG. 1A in accordance with the principles of the invention.

FIG. 4 illustrates a second exemplary control means for controlling the expansion of inter-vivos tube 100, in accordance with the principles of the invention.

In this illustrated embodiment inter-vivos tube 100 is shown in a contracted configuration as previously discussed with regard to FIG. 1A.

Further illustrated is cap element 220, flange element 215 and membrane 240, through which inter-vivos tube 100 may be inserted to provide an air-tight seal between cap 220 and inter-vivos tube 100, as previously described.

Furthermore, cap 220 may be placed onto tube inter-vivos tube 100 and secured in place by, for example, tape or a VELCRO type connector 485. Alternatively, cap 220 and inter-vivos tube 100 may be integrated together.

Further illustrated is expansion control element 400, which is similar to expansion control element 300, previously discussed.

Expansion control element 400 is insertable into cap element 220, to apply a downward force, through ridge or ring element 310, onto a top edge of sliding mechanism 145.

Expansion control element 400 further includes a second flange element 415 circumventing expansion control element 400.

Further illustrated are screws 420 and 422, on diametrically opposed sides of cap 220 extending through flange element 415.

Screws 420 and 422, passthrough through threaded holes 430, 432, respectively in flange 415 and engage holes 440, 442, respectively within flange 215. The holes 440 and 442 within flange 215 are referred to as capture or blind holes, wherein screws 420, 422, are contained within the holes 440, 442, respectively, while being free to rotate therein.

Further illustrated is handle 450 on screw 420. Handle 450 allows for the turning of corresponding screw 420. Although only one handle is discussed, it would be appreciated that a similar handle 452 may be utilized on screw 422.

In accordance with the principles of the invention, as screw handle 450 is turned, screw 420, in thread hole 430, causes expansion control element 400 to move downward as control element 400 rides downward on screws 420, 422. With the continued turning of handle 450, expansion control element 400 is moved downward and ridge or ring element 310 engages a top (or proximal) edge of slider 145 to cause slider 145 to move downward; effectively expanding the circumference of inter-vivos tube 100.

In accordance with the principles of the invention, screw element 422, for example, may further include a calibrated gauge (i.e., special markings 475) that provide an indication of the degree of expansion of slit 130 and consequently, of inter-vivos tube 100.

Although screw element 422 is discussed as including a screw thread and passing through a threaded hole 432, it would be recognized that screw element 422 may be comprise a non-threaded rod passing through a non-treaded hole 432. In this manner, screw element 422, constructed as a smooth rod, may merely provide stabilization of cap element 400 as handle 450 is turned and corresponding screw element 420 causes cap element 400 to move in a downward direction.

In accordance with another aspect the invention, ridge 310 may be fused with or retained to top edge of sliding mechanism 145. In this case, as screw 420 is rotated in a counter-clockwise direction] sliding mechanism 145 is moved upward to effectively reduce the size of inter-vivos tube 100. This, while advantageous in the removal of inter-vivos tube 100 from a patient, is an optional feature of the invention claimed.

Figure 5:
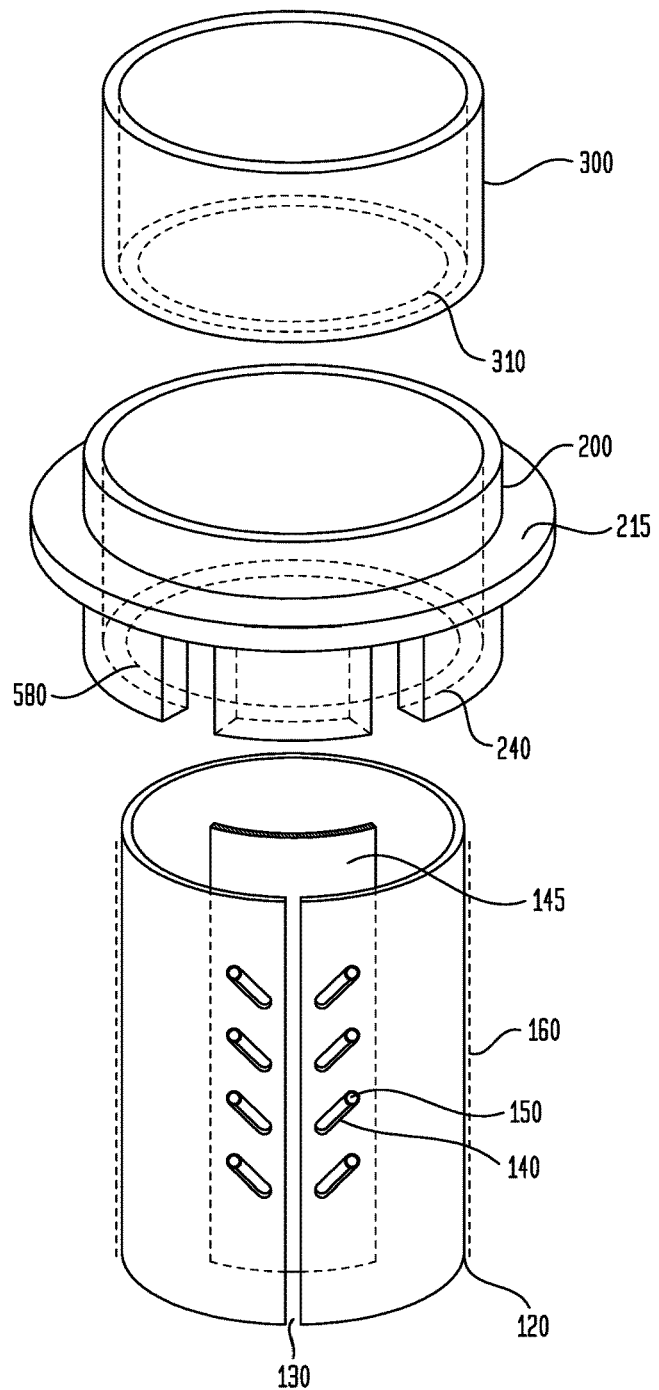
FIG. 5 illustrates a perspective view of another aspect of the exemplary control system shown in FIG. 3.

FIG. 5 illustrates another aspect of the invention claimed in FIG. 3, wherein cap element 220 is integrated onto inter-vivos tube 100, such that expandable membrane 160 surrounding inter-vivos tube 100 further encapsulates a lower or distal end of cap 220.

In this illustrated embodiment, where cap 220 is integrated onto a proximal end 110 of inter-vivos tube 100, the expansion control 300/400 (shown in FIGS. 3 and 4) operates to control the expansion of inter-vivos tube 100, as previously discussed.

In accordance with a principles of this aspect of the invention, a lower or distal end of cap element 220 may include a plurality of slits 580, extending downward, placed along a circumference of the distal end of cap 200. The plurality of slits 580 create a plurality of "fingers" between adjacent ones of the plurality of slits 580. The plurality of slits 580 (or fingers) allow for the expansion of the distal end of cap element 220 to accommodate the expansion of the inter-vivos tube 100.

In accordance with this aspect of the invention, expansion control 300 (400) engage a top edge of slider 145, as previously discussed and slits 580 in lower end of cap 220 expand as inter-vivos tube 100 expands. The elastic, flexible and expandable membrane 160 continues to retain an air-tight seal between cap 220 and the expanded inter-vivos tube 100.

As it is important to protect the tracheal wall from the points or open ends of the nipples 150 protruding through a corresponding slot 140, the protruding or open ends must be made as smooth as possible.

Figure 6A:
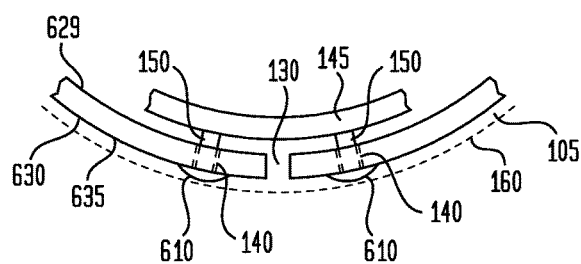
FIG. 6A illustrates a top cross-sectional view of a first exemplary embodiment of the incorporation of a pin (nipple or nib) in a corresponding slot or groove in an inter-vivos tube in accordance with the principles of the invention.

FIG. 6A illustrates a cross-sectional view of the top of tube element 105 incorporating a first embodiment of nipple 150 in accordance with the principles of the invention.

In this illustrated embodiment, the sliding mechanism 145 is illustrated within tube element 105, as previously discussed. Further illustrated is expandable membrane 160 surrounding tube element 105.

Further illustrated are nipples 150 extending from sliding mechanism 145 though corresponding slots 140 on opposite sides of slit 130 in tube element 105. Nipples 150, initiated on slider 145, extend through corresponding slot 140 toward an outer surface 630 of wall 635 of tube element 105. In this illustrated embodiment, a free end of nipples 150, exiting corresponding slot 140, are smoothed, resulting in bumps 610, along outer surface 630. Bumps 610 retain nipple 150 in slot 140 as nipple 150 moves from a proximal end of slot 140 to a distal end of slot 140 (see FIGS. 1A and 1B).

The smoothed free end 610 of nipple 150 is advantageous as it removes sharp or jagged ends from scratching delicate tissues within the trachea.

Smoothing of the free end of nipple 150 may, for example, be obtained by heat treating the free end.

Figure 6B:
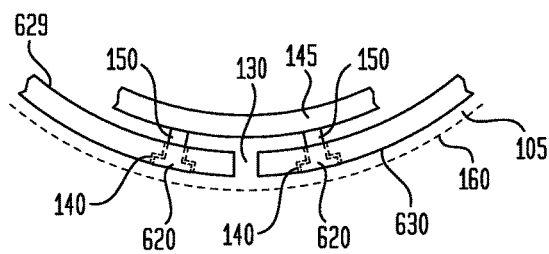
FIG. 6B illustrates a top cross-sectional view of a second exemplary embodiment of the incorporation of a pin (nipple or nib) in a corresponding slot or groove in an inter-vivos tube in accordance with the principles of the invention.

FIG. 6B illustrates a cross-section view of a top the tube element 105 incorporating a second embodiment of nipple 150 in accordance with the principles of the invention.

In this illustrated embodiment, the sliding mechanism 145 is illustrated positioned along an interior surface 629 of tube element 105, as previously discussed. Further illustrated is expandable membrane 160 surrounding tube element 105.

In accordance with the principles of the invention, the slot 140 is formed of two concentric openings. The first extending from an inner surface 629 to an outer surface 630 of wall element 635 and a second extending from the outer surface 630 toward, but not extending to, the interior surface 629 of wall 635. The diameter of the second opening being greater than the diameter of the first opening.

Nipple 150, extending through slot 140 may then be heated such that a flattened free end of nipple 150, to create a 'slidable' nail-head-like peg slider with a substantially flat head 620, remains in the second, larger, sized opening associated with slot 140/

Alternatively, a molding process may be applied to the nipples 150 extending through slot 140 to create a 'slidable' nail-head-like peg slider with a substantially flat head 620. That is, the nipple or spike 150 is shaped as a nail having a substantially flat head and a shank—the shank extending from the slider 145 and the head included within the larger second opening in slot 140.

In this manner, the outer surface 630 of tube 105 is essentially smooth. Again, avoiding any sharp or jagged edges from scratching or damaging delicate tissues within the trachea.

In another aspect of the invention a portion of inter-vivos tube element 105 containing slots 140 may be thickened to enable the nail-head-like peg slider 150 to be contained within the tube element 105. Thus, the outer surface 630 of tube element 105 remains essentially smooth.

As previously discussed, the inter-vivos tube 100 may be covered by an expandable membrane 160 to prevent air leakage and further provides smooth surface that allows for unhindered insertion of ETT 100 into a sedated patient.

FIG. 7 illustrates a cross-sectional view of an inter-vivos tube 100, along a longitudinal axis of tube element 105, in accordance with another aspect of the invention.

In this illustrated embodiment, inter-vivos tube 100 comprises a slit 130 (not shown) and sliding mechanism 700, which is comparable to the sliding mechanism 145, previously discussed.

In this exemplary embodiment, sliding mechanism comprises sliding mechanism 145 and a second element 710 positioned along an outsider surface 630 of tube element 105. Second element 710 is fused at a top edge 720 of sliding mechanism 145 to form slider 700. Second element 710 captures or prevents free edges of nipples 150, extending through slots 140 from extending into (optional element) flexible membrane 160 and contact delicate tissue in the trachea.

Figure 8:
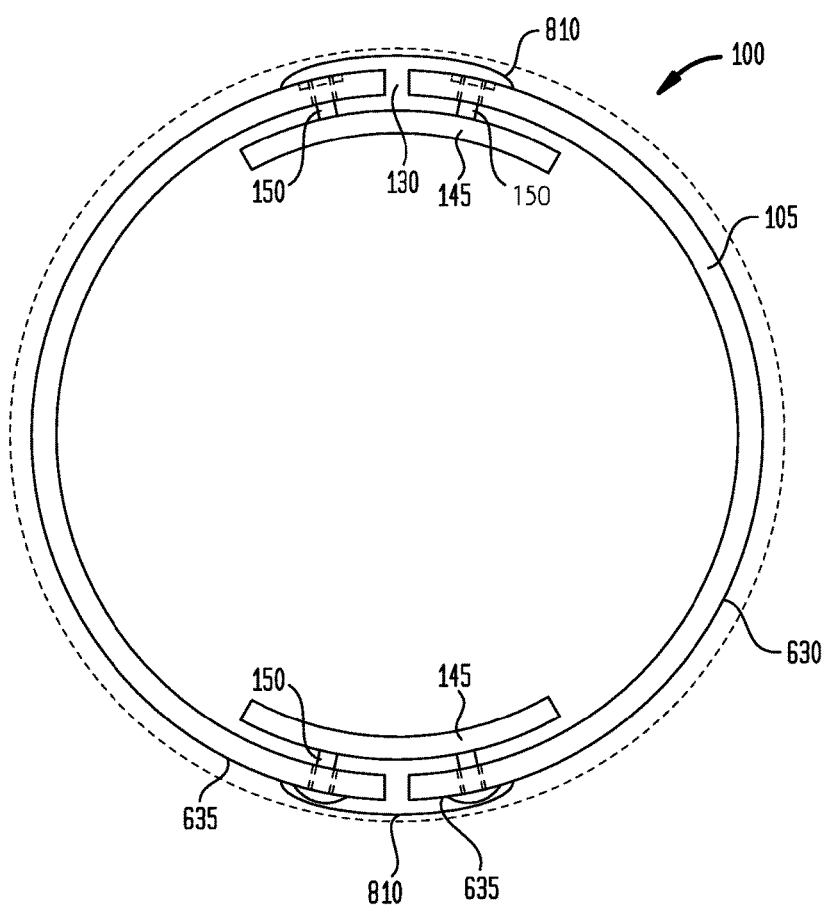
FIG. 8 illustrates a top-cross-sectional view of a second embodiment of an inter-vivos tube in accordance with the principles of the invention.

FIG. 8 illustrates a cross-sectional view, perpendicular to the longitudinal axis of tube element 105, of the inter-vivos tube 100 in accordance with the principles of the invention.

In this illustrated embodiment, which is similar to the invention shown in FIGS. 6A and 6B, showing two slits 130, and corresponding sliding mechanisms 145 including nipples 150 extending through slots 140 in tube element 105.

Further illustrated, is a second flexible or expandable member 810 attached to tube element 105 on opposing sides of a corresponding slit 130. The second membrane 810, similar to the expandable membrane 160 is further attached to the proximal end 110 and the distal end 120 of tube element 105.

Second membrane 810 provides additional support for retaining air within inter-vivos tube 100 as the slit(s) 130 in tube element 105 is (are) expanded.

Figure 9:
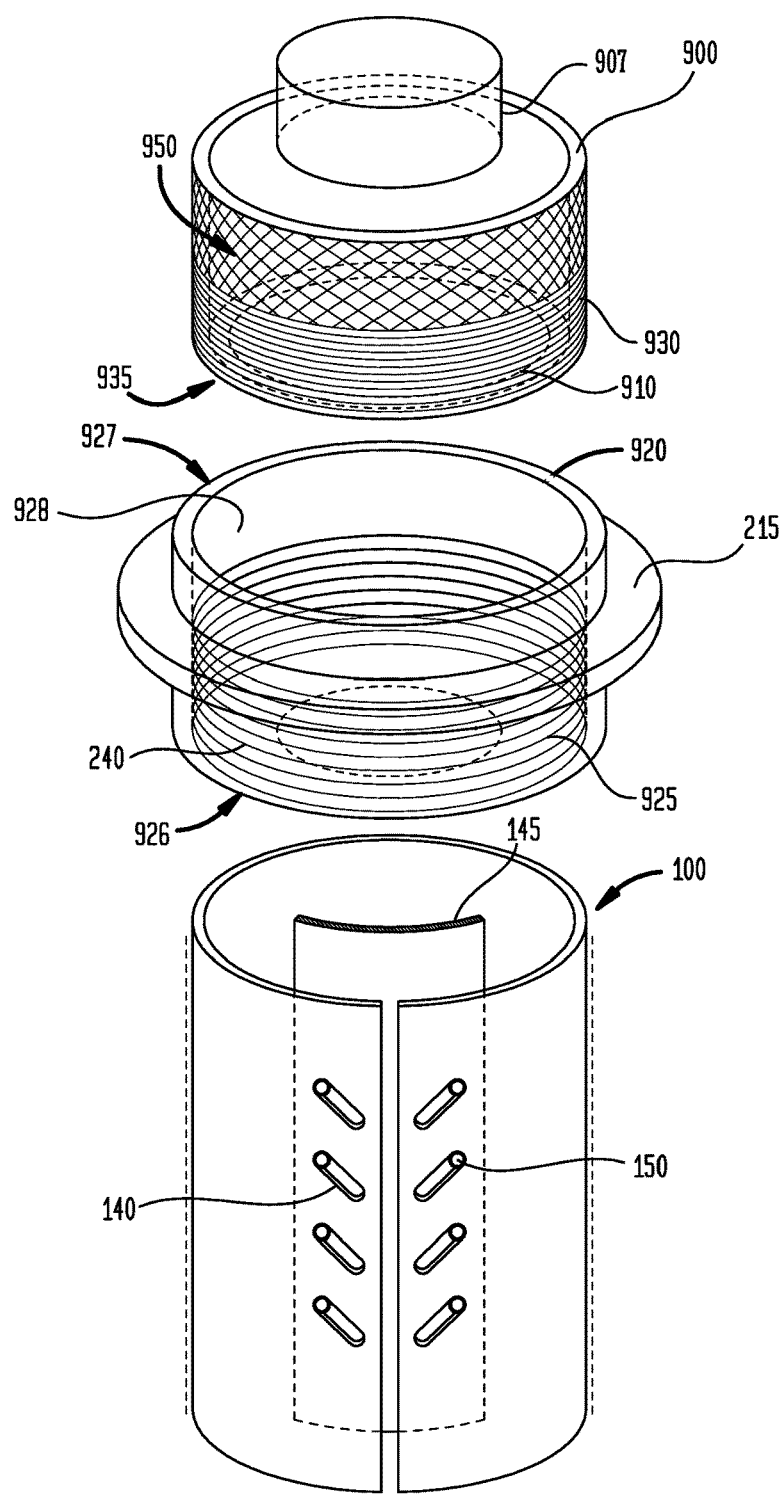
FIG. 9 illustrates a perspective view of a third exemplary embodiment of a control system for controlling the expansion of the inter-vivos tube shown in FIG. 1A in accordance with the principles of the invention.

FIG. 9 illustrates a perspective view of a fifth exemplary embodiment of an expanding control system incorporating the inter-vivos tube shown in FIG. 1A, 1B in accordance with the principles of the invention.

In this illustrated embodiment, which includes the inter-vivos tube 100, containing at least one slit 130 and slots 140 within tube element 105 and nipples 150, incorporated onto slider 145, passing through slots 140, as previously disclosed.

In this illustrated embodiment, cap element 920 includes flange element 215, similar to the flange discussed with regard to FIG. 3. In addition, cap element 920 may represent a separate element, similar to that shown in FIG. 3, wherein cap element 920 may be placed onto inter-vivos tube 100 and held in place by tape or other retaining means (e.g., VELCRO), as previously discussed. Alternatively, cap element 920 may be integrated onto a proximal end of inter-vivos tube 100, as discussed with regard to FIG. 5.

In addition, cap element 920 includes a screw thread 925 positioned circumferentially along an interior surface 928. Screw thread 925 extends from substantially a distal end 926 of cap element 920 toward the proximal end 927 of cap element 920. Screw thread 925 may cover a portion of the interior surface 928 of cap element 920 or the entire interior surface 928 of cap element 920.

Further shown is expansion control element 900, similar to expansion control element 300 shown in FIG. 3. In this illustrated case, the expansion control element 900 includes an internal ridge 910 at substantially a distal end 935 of expansion control element 900. The internal ridge 910 is configured to contact a proximal end of slider 145 similar to internal ridge 310 shown in FIG. 3.

In this illustrated embodiment, screw thread 930 is incorporated circumferentially along an outer surface of expansion control 900. Screw thread 930 matches screw thread 925, such that expansion control element 900 may be rotated within cap element 920 to apply a downward force on a proximal end of slider 145.

Thus, expansion control element (referred to as rotator) 900 provides a controlled means to cause inter-vivos tube 100 to expand as rotator 900 rotationally engages the screw thread 925 of cap element 920.

Rotator 900 further provides a means 907 (e.g., an adapter) for engaging a conventional air supply tube through which air or gas may be provided to a patient, similar to that discussed with regard to FIG. 3.

In another aspect of the invention, rotator 900 may include a knurl section 950. Knurl section 950 is advantageous to provide a surface that prevents finger slippage during rotation.

As would be recognized, inter-vivos tube 100 may be constructed of conventional material, known and used, in existing inter-vivos or ETTs. Similarly, slider 145 may be constructed of materials similar to those of conventional stents, used in the medical profession. For example, the slider material may be of a silicone and/or plastic material. The material selected for slider 145 may further be self-lubricating to facilitate the sliding of slider 145. The material selected for slider 145 (and the tube element 105) may further include a "memory" that allows for an interior curvature of the slider 145 and inter-vivos tube element 105 to facilitate insertion of inter-vivos tube 100.

In accordance with the principles of the invention, the membrane 160, while being of a conventional type material to expand as inter-vivos tube 100 is expanded, may be constructed of a material that includes a "memory," which causes the membrane 160 to return to its original position when forces that expand the membrane are removed. That is, the membrane 160, which is subjected to expansion forces as inter-vivos tube 100 is expanded, may apply a retracting force onto inter-vivos tube 100 as the downward force, which causes inter-vivos tube 100 to expand, is removed.

In this case, the membrane 160 may provide dual purpose of providing an air-tight seal for the expanding inter-vivos tube and a means for reducing the expanded diameter of inter-vivos tube 100 when inter-vivos tube 100 is to be removed.

In summary, an expandable inter-vivos tube is disclosed that comprises a slit formed longitudinally within a tube, wherein slots on opposing sides of the slit are oriented at an acute angle with response to a distal end of the tube. Further disclosed is a slidable mechanism that slides along an interior surface of the inter-vivos tube wherein nipples, on the slidable mechanism, engage a corresponding one of the slots. As the slidable mechanism is pushed downward, the nipples slide from a proximal end of a corresponding slot to a distal end of the corresponding slot. The changing position of the nipple or tab within a corresponding slot causes an expansion of the slit and consequently an increase the diameter of inter-vivos tube.

Further disclosed are means for sliding the sliding mechanism downward to increase the diameter of the inter-vivos tube. For example, the control means for causing the sliding of the sliding mechanism may be cap simply pushing downward, or causing downward movement in a turning (i.e., screwing) manner. The screwing manner may be external, or internal, to the cap through which the inter-vivos-tube engages.

Although the present invention has been described with regard to an inter-vivos tube, it would be recognized that the mechanism for expanding tubes suitable for catheters or stents are considered to be within the scope of the invention.

The invention has been described with reference to specific embodiments. One of ordinary skill in the art, however, appreciates that various modifications and changes can be made without departing from the scope of the invention as set forth in the claims. Accordingly, the specification is to be regarded in an illustrative manner, rather than with a restrictive view, and all such modifications are intended to be included within the scope of the invention.

Benefits, other advantages, and solutions to problems have been described above with regard to specific embodiments. The benefits, advantages, and solutions to problems, and any element(s) that may cause any benefits, advantages, or solutions to occur or become more pronounced, are not to be construed as a critical, required, or an essential feature or element of any or all of the claims.

As used herein, the terms "comprises", "comprising", "includes", "including", "has", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus.

In addition, unless expressly stated to the contrary, the term "of" refers to an inclusive "or" and not to an exclusive "or". For example, a condition A or B is satisfied by any one of the following: A is true (or present) and B is false (or not present); A is false (or not present) and B is true (or present); and both A and B are true (or present).

The terms "a" or "an" as used herein are to describe elements and components of the invention. This is done for convenience to the reader and to provide a general sense of the invention. The use of these terms in the description herein should be read and understood to include one or at least one. In addition, the singular also includes the plural unless indicated to the contrary. For example, reference to a composition containing "a compound" includes one or more compounds. As used in this specification and the appended claims, the term "or" is generally employed in its sense including "and/or" unless the content clearly dictates otherwise.

All numeric values are herein assumed to be modified by the term "about," whether or not explicitly indicated. The term "about" generally refers to a range of numbers that one of skill in the art would consider equivalent to the recited value (i.e., having the same function or result). In any instances, the terms "about" may include numbers that are rounded (or lowered) to the nearest significant figure. It is expressly intended that all combinations of those elements that perform substantially the same function in substantially the same way to achieve the same results are within the scope of the invention. Substitutions of elements from one described embodiment to another are also fully intended and contemplated.

What is claimed is:

1. An expandable inter-vivos tube comprising:
    a tube element comprising:
        at least one slit extending along a longitudinal axis of the tube element from a proximal end to a distal end of the tube element;
        a plurality of slots positioned along an edge of each of the at least one slit, each slot arranged at an angle with respect to the longitudinal axis;
    a slider associated with, and spanning across each of the at least one slit, the slider, arranged along an inner surface of the tube element, extending along the longitudinal axis toward the distal end, said slider comprising:
        an edge element configured to be positioned outside the proximal end of the tube element; and
        a plurality of nipples, each of the nipples engaging a corresponding one of the plurality of slots, wherein each nipple extends from the inner surface of the tube element through a corresponding one of the plurality of slots toward an outer surface of the tube element.

2. The expandable inter-vivos tube of claim 1, further comprising:
    an expandable membrane enclosing the tube element, wherein the expandable membrane is attached at the proximal end and at the distal end of the tube element.

3. The expandable inter-vivos tube of claim 1, further comprising:
    an expandable membrane, attached from the proximal end to the distal end of the tube element, spanning across a corresponding one of the at least one slit.

4. The expandable inter-vivos tube of claim 1, further comprising:
    a flange element integrally incorporated onto the tube element, substantially toward the proximal end of tube element.

5. The expandable inter-vivos tube of claim 1, wherein the slider comprises:
    a second slider arranged along an outer surface of the tube element and spanning a corresponding one of the at least one slit, the second slider comprising:
    an edge element attached to the edge of the slider;
    wherein the plurality of nipples of the slider are contained between the slider and the second slider.

6. The expandable inter-vivos tube of claim 1, further comprising:
    a cap element comprising:
        a flange element positioned substantially toward a proximal end of the cap element; and
        an expandable membrane, positioned at a distal end of the cap element, comprising:
        a central opening into which the tube element is configured to be inserted.

7. The expandable inter vivos tube of claim 6, wherein the cap element is one of: attached to the proximal end of the tube element and positionable on the proximal end of the tube element.

8. The expandable inter-vivos tube of claim 6, wherein the cap element comprises:
   an internal ridge element configured to contact of the edge of the slider.

9. The expandable inter-vivos tube of claim 6, further comprising:
   an expansion control element insertable into the cap element.

10. The expandable inter-vivos tube of claim 9, wherein the expansion control element comprises:
    a screw thread extending along a circumference of the expansion control element.

11. The expandable inter-vivos tube of claim 10, wherein the cap element comprises:
    a screw thread extending circumferentially along an interior surface of the cap element.

12. The expandable inter-vivos tube of claim 9, wherein the expansion control element comprises:
    a flange element circumventing the expansion control element, said flange element comprising at least one threaded passthrough, wherein
    the flange element of the cap element comprises corresponding blind holes; and
    a screw extending between the at least one threaded passthrough and a corresponding blind hole.

13. The expandable inter-vivos tube of claim 1, each slot comprising:
    a first opening extending from an inner surface of the tube element to an outer surface of the tube element; and
    a second opening extending from the outer surface of the tube element toward the inner surface of the tube element, wherein a diameter of the second opening is greater than a diameter of the first opening.

14. The expandable inter-vivos tube of claim 9, wherein the expansion control element comprises:
    a flange element circumscribing the expansion control element, said flange element comprising at least one threaded passthrough, wherein
    the flange element of the cap element comprises corresponding blind holes; and
    a screw extending between the at least one threaded passthrough and a corresponding blind hole.

15. An expandable inter-vivos tube system comprising:
    an adapter comprising:
       a flange element arranged circumferentially along an outer surface;
       a thread element arranged circumferentially along an inner surface; and
       an expandable membrane comprising a center hole spanning a distal end;
    an expandable inter-vivos tube, configured to engage the expandable membrane, comprising:
       a tube element comprising:
          at least one slit extending along a longitudinal axis of the tube element from a proximal end to a distal end of the tube element;
          a plurality of slots positioned along an edge of each of the at least one slit, each slot arranged at an angle with respect to the longitudinal axis;
       a slider associated with, and spanning across each of the at least one slit, the slider being arranged along an inner surface of the tube element along the longitudinal axis toward the distal end, said slider comprising:
          an edge configured to be positioned outside the proximal end of the tube element; and
          a plurality of nipples, each of the nipples engaging a corresponding one of the plurality of slots, wherein each nipple extends from the inner surface of the tube element through a corresponding one of the plurality of slots toward an outer surface of the tube element; and
    a rotator comprising:
       a screw thread circumferentially along an outer surface; and
       an interior ridge element configured to engage said edge.

16. The expandable inter-vivos tube system according to claim 15, wherein the adapter is one of: integrated onto a proximal end of the inter-vivos tube and positionable onto a proximal end of the inter-vivos tube.

17. The expandable inter-vivos tube system according to claim 15, further comprising:
    an expandable membrane surrounding at least the inter-vivos tube.

* * * * *